(12) United States Patent
Kim et al.

(10) Patent No.: US 10,801,960 B2
(45) Date of Patent: Oct. 13, 2020

(54) METHODS FOR DETECTING ENDOCRINE DISRUPTORS USING DUAL MODES OF COLORIMETRIC AND FLUOROMETRIC ANALYSIS

(71) Applicant: INDUSTRY-UNIVERSITY COOPERATION FOUNDATION HANYANG UNIVERSITY, Seoul (KR)

(72) Inventors: Young Pil Kim, Seoul (KR); Myung Chan Gye, Gyeonggi-do (KR); Eunsong Lee, Gyeonggi-do (KR); Gae Baik Kim, Seoul (KR)

(73) Assignee: INDUSTRY-UNIVERSITY COOPERATION FOUNDATION HANYANG UNIVERSITY (KR)

( * ) Notice: Subject to any disclaimer, the term of this patent is extended or adjusted under 35 U.S.C. 154(b) by 261 days.

(21) Appl. No.: 15/884,868

(22) Filed: Jan. 31, 2018

(65) Prior Publication Data

US 2018/0217062 A1  Aug. 2, 2018

(30) Foreign Application Priority Data

Jan. 31, 2017  (KR) .................. 10-2017-0013847
Jun. 5, 2017  (KR) .................. 10-2017-0069609

(51) Int. Cl.

| G01N 21/64 | (2006.01) |
|---|---|
| G01N 21/31 | (2006.01) |
| G01N 33/53 | (2006.01) |
| G01N 33/58 | (2006.01) |
| G01N 21/17 | (2006.01) |

(52) U.S. Cl.
CPC .......... *G01N 21/643* (2013.01); *G01N 21/31* (2013.01); *G01N 21/6428* (2013.01); *G01N 21/6486* (2013.01); *G01N 33/5308* (2013.01); *G01N 33/582* (2013.01); *G01N 33/587* (2013.01); *G01N 21/6452* (2013.01); *G01N 2021/174* (2013.01); *G01N 2021/6432* (2013.01); *G01N 2021/6491* (2013.01)

(58) Field of Classification Search
CPC ..... G01N 2021/174; G01N 2021/6432; G01N 2021/6491; G01N 21/31; G01N 21/6428; G01N 21/643; G01N 21/6452; G01N 21/6486; G01N 21/5308; G01N 21/582; G01N 21/587; G01N 33/5308; G01N 33/582; G01N 33/587
USPC .............. 436/131, 164, 171, 172; 422/82.05, 422/82.08, 82.09
See application file for complete search history.

(56) References Cited

U.S. PATENT DOCUMENTS

| 7,892,734 B2* | 2/2011 | Lu .................... C12Q 1/6818 |
|---|---|---|
| | | 435/6.11 |
| 2005/0059042 A1* | 3/2005 | Rothberg .................. B82Y 5/00 |
| | | 435/6.14 |

(Continued)

OTHER PUBLICATIONS

Lee et al. Sensors and Actuators B: Chemical, vol. 260, pp. 371-379, Jan. 3, 2018.*

(Continued)

*Primary Examiner* — Maureen Wallenhorst
(74) *Attorney, Agent, or Firm* — Adsero IP

(57) ABSTRACT

Provided herein is a method of effectively quantifying a target material by performing both colorimetry and fluorescence analysis on the same sample, based on metal nanoparticles and an aptamer.

9 Claims, 6 Drawing Sheets

(56) References Cited

U.S. PATENT DOCUMENTS

2015/0247874 A1* 9/2015 Chavez Benavides ..................... G01N 33/946
436/501
2017/0234874 A1* 8/2017 Adams ................. G01N 21/553
435/7.21

OTHER PUBLICATIONS

Duan et al. Talanta, vol. 180, pp. 76-80, Dec. 13, 2017.*
Ragavan et al. Chem. Communication, vol. 49, pp. 5960-5962, 2013.*
Ni et al. Analytical Biochemistry, vol. 523, pp. 17-23, Jan. 27, 2017.*
ENGE 2016, International Conference on Electronic Materials and Nanotechnology for Green Environment, Nov. 6-9, 2016, Ramada Plaza Jeju Hotel, Jeju, South Korea, www.enge2016.org; Lee et al., "Fluorescing Aptamer-Gold Nanoparticle Complex for the Sensitive Detection of Bisphenol A", 3 pages.
Lv et al., "Aptamer-based fluorescent detection of ochratoxin A by quenching of gold nanoparticles", RSC Adv., 2017, 7, 16290, 5 pages.
Ragavan et al., "Sensors and biosensors for analysis of bisphenol-A", Trends in Analytical Chemistry 52 (2013) 248-260.

* cited by examiner

[FIG. 1]
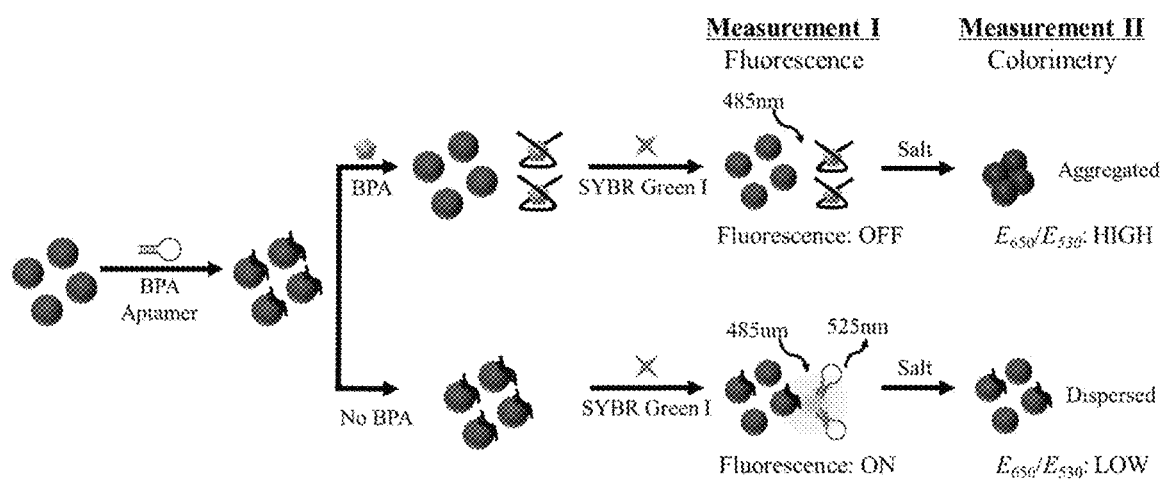
[FIG. 2]
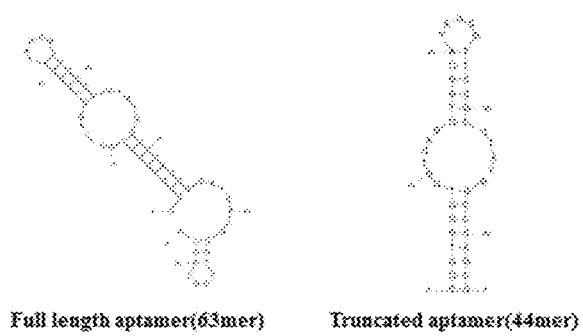
Full length aptamer(63mer)　　Truncated aptamer(44mer)

[FIG. 3]
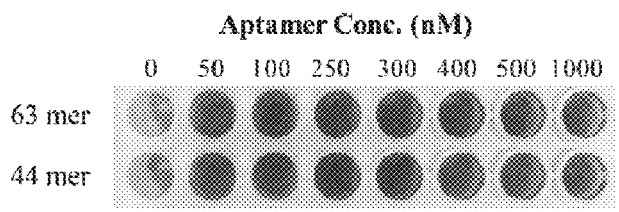
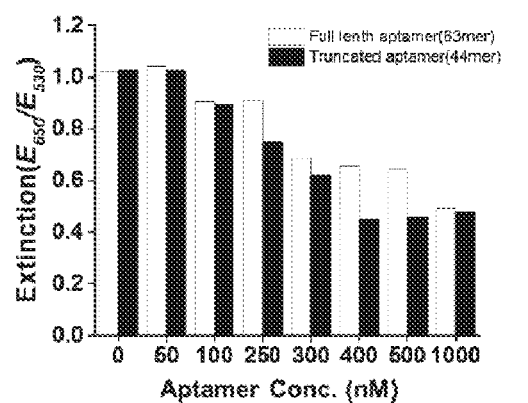
[FIG. 4]
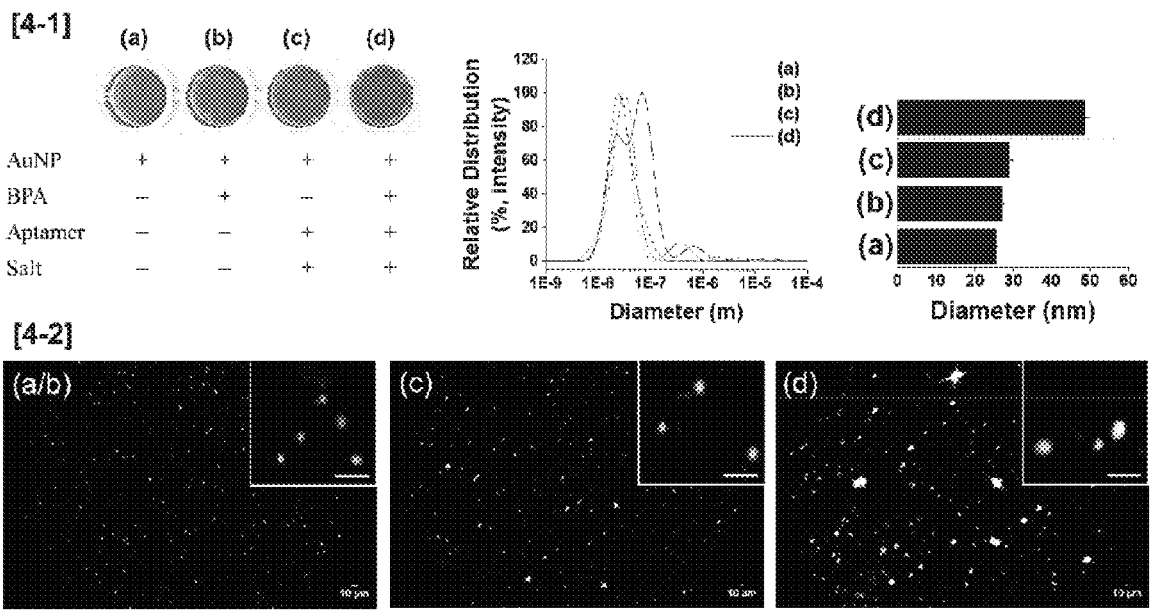

[FIG. 5]
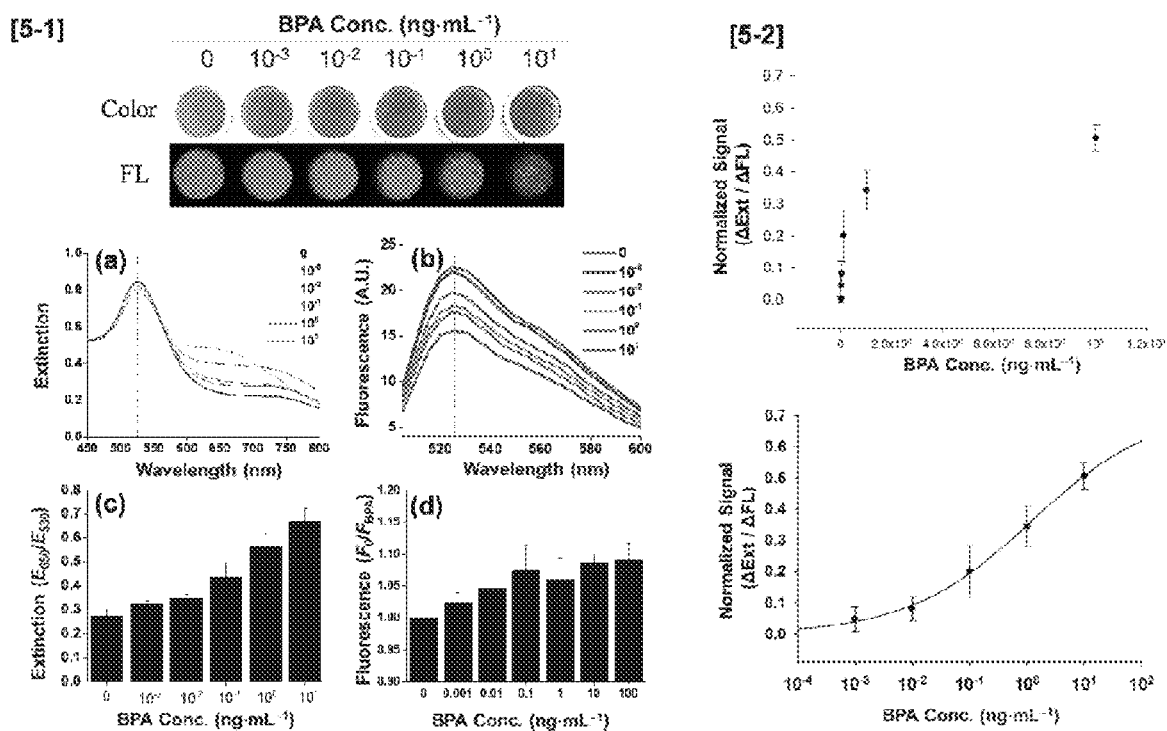
[FIG. 6]
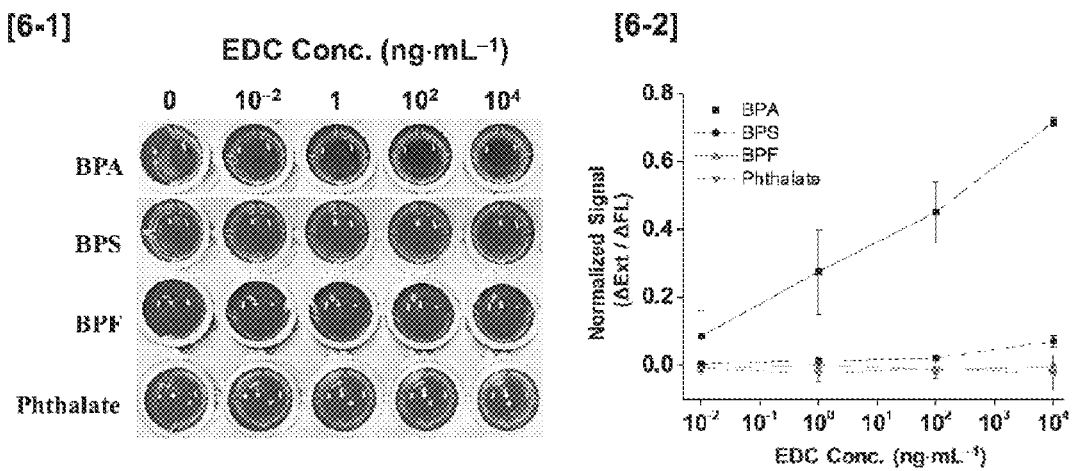

[FIG. 7]
[7-1]
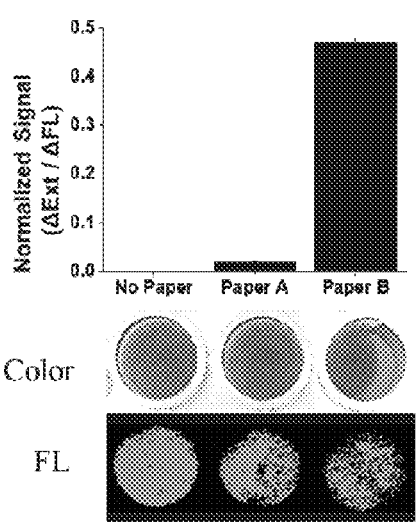
[7-2]
| Sample | BPA Conc. | | RSD (%) =100× ((b/a)·10⁴) |
|---|---|---|---|
| | ªHPLC (μg·mL⁻¹) | ᵇApt/AuNP (10⁻⁴·μg·mL⁻¹) | |
| Paper A | N/D | N/D | - |
| Paper B | 66.8±0.6 | 63.3±7.9 | 102.4±11.8 |
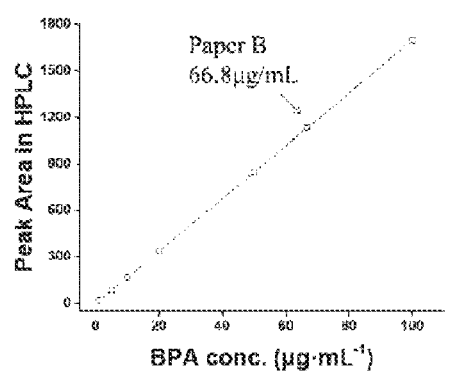

[FIG. 8]
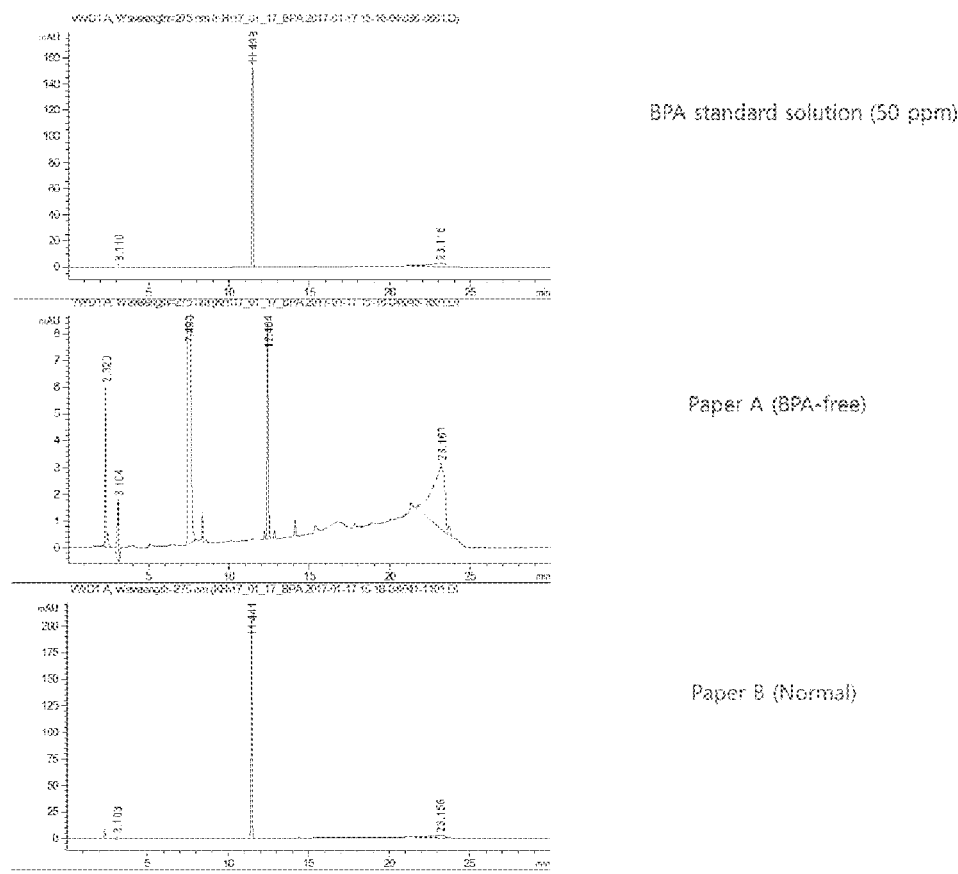
[FIG. 9]
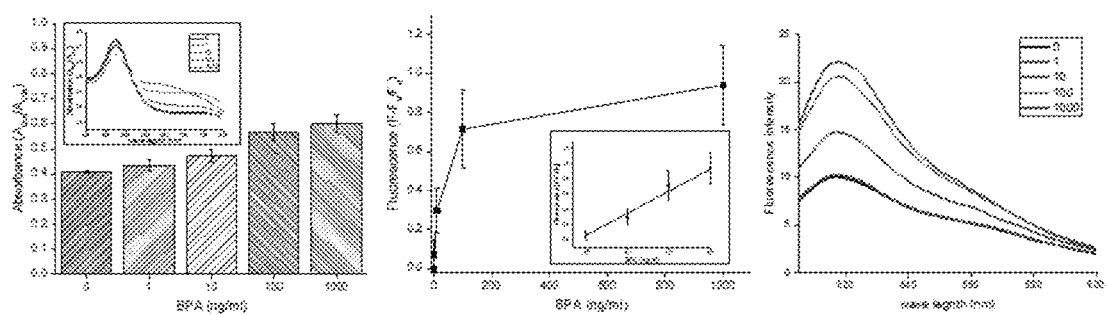

[FIG. 10]
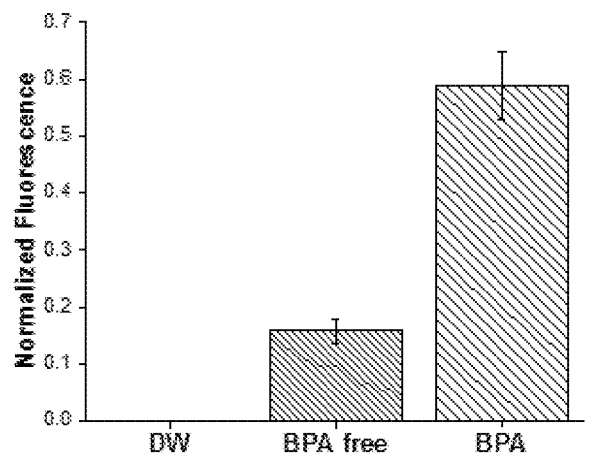
[FIG. 11]
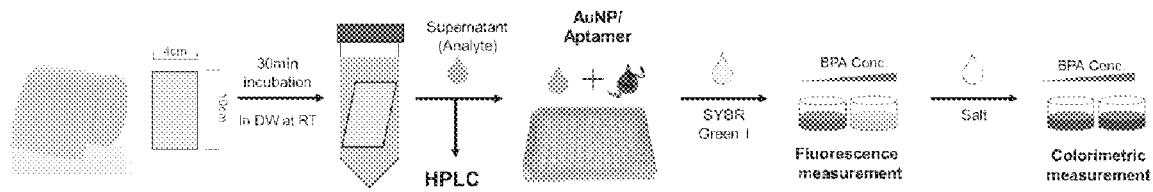

METHODS FOR DETECTING ENDOCRINE DISRUPTORS USING DUAL MODES OF COLORIMETRIC AND FLUOROMETRIC ANALYSIS

CROSS-REFERENCE TO RELATED APPLICATIONS

This application claims priority to and the benefit of Korean Patent Application No. 2017-0013847, filed on Jan. 31, 2017 and Korean Patent Application No. 2017-0069609, filed on Jun. 5, 2017, the disclosures of which are incorporated herein by reference in their entirety.

BACKGROUND

1. Field of the Invention

The present disclosure relates to a method of detecting and quantifying a target material.

2. Discussion of Related Art

Bisphenol A, which is a type of environmental hormone, is a substance commonly contained in plastic plasticizers, coating agents of thermal transfer paper, and inner coatings of canned drinks. When the bisphenol A is introduced into the human body at a high concentration, the bisphenol A interferes with sexual hormone metabolism, and thus harmfully affects the human body, and therefore, a more prompt and accurate measurement method is required.

As a standard measurement method, the LC/GC-MS method provides a most accurate sample analysis, but is excessively time-consuming when analyzing a sample and has difficulty in analyzing a sample according to processes, and thus methods of overcoming these drawbacks have been developed.

As a representative method for rapid analysis, a gold nanoparticle colorimetric method has been developed (see Non-Patent Document 1). This method can easily detect a sample through color change, but may have significantly low sensitivity. In addition, aptamer- and antibody-based fluorescence analysis is disadvantageous in that accuracy is low due to fluorescence interference by a sample. In addition, as a method of measuring low molecular weight materials other than bisphenols, cases in which colorimetric and fluorometric methods are simultaneously used for measurement, by using gold nanoparticles and an aptamer have been reported (Non-Patent Document 2). However, when the termini of DNA aptamer is labeled with fluorescence, binding between the aptamer and a target may be affected by the labeled fluorescent material, and it is difficult to effectively amplify a fluorescence signal.

NON-PATENT REFERENCES

1. Trends in Analytical Chemistry 52 (2013) 248-260
2. RSC Advances, 2017, 7, 16290

SUMMARY OF THE INVENTION

The present disclosure aims to consecutively perform fluorescence analysis and color changes on the same sample, based on structural changes of gold nanoparticles and an aptamer.

That is, the present disclosure aims to detect and quantify a target material present in a sample by performing colorimetry and fluorescence analysis on the same sample, based on gold nanoparticles and an aptamer.

According to an aspect of an embodiment, there is provided a method of effectively detecting and quantifying a target material present in a sample by performing colorimetry and fluorescence analysis on the same sample, based on gold nanoparticles and an aptamer.

The method according to the present disclosure uses a dye material that binds to an aptamer to thereby generate fluorescence, and thus binding between the aptamer and a target is not affected by the fluorescent material and a fluorescence signal may be more effectively amplified, when compared to an existing method in which the termini of an aptamer is directly labeled with fluorescence.

In particular, when the method according to the present disclosure is used to detect and quantify bisphenol A, which is a type of environmental hormone, it is possible to perform measurement with high sensitivity within a short period of time compared to a method depending on either a colorimetric method or a fluorescence method.

BRIEF DESCRIPTION OF THE DRAWINGS

The above and other objects, features and advantages of the present disclosure will become more apparent to those of ordinary skill in the art by describing in detail exemplary embodiments thereof with reference to the accompanying drawings, in which:

FIG. 1 is a diagram illustrating a method of detecting bisphenol A (BPA), according to the present disclosure;

FIG. 2 illustrates BPA aptamers used in examples of the present disclosure;

FIG. 3 illustrates examination results of the suitability of a concentration ratio of each of the aptamers and gold nanoparticles according to the method of the present disclosure;

FIG. 4 illustrates results of reaction of an aptamer-gold nanoparticle complex with respect to BPA;

FIG. 5 illustrates quantitative analysis results of BPA according to the method of the present disclosure;

FIG. 6 illustrates examination results of BPA specificity according to the method of the present disclosure;

FIG. 7 illustrates detection results of BPA included in a receipt according to the method of the present disclosure;

FIG. 8 illustrates high-performance liquid chromatography (HPLC) data for measurement of the amount of BPA included in a receipt according to the method of the present disclosure;

FIG. 9 illustrates measurement results of BPA using an FAM-aptamer,

FIG. 10 illustrates detection results of BPA included in a receipt using an FAM-aptamer; and FIG. 11 is a diagram illustrating processes of preparing and measuring a receipt sample.

DETAILED DESCRIPTION OF EXEMPLARY EMBODIMENTS

Hereinafter, the present invention will be described with reference to examples and comparative examples in detail. However, the present invention is not limited to these examples.

The present disclosure relates to a method of detecting a target material.

The method of detecting a target material, according to the present disclosure, includes: (A) reacting a sample including a target material with an aptamer-metal nanoparticle complex;

(B) adding a fluorescent dye to the reaction product of process (A) and measuring fluorescence; and (C) adding a salt to the reaction product of process (B) and measuring absorbance.

In the present disclosure, a colorimetric method and fluorescence analysis may be applied to the same sample. As used herein, the colorimetric method refers to testing or quantification of the concentration of a chemical compound or a solution by measuring absorbance of light having a particular wavelength by using a color reagent or the like. In addition, the fluorescence analysis, which is a chemical analysis method using the fluorescence of a material, refers to analysis of the fluorescence of a fluorescent material into which a sample as a non-fluorescent material is converted by chemical reaction.

In other words, in the present disclosure, a target material present in a sample may be effectively and highly accurately detected and quantified within a short period of time by simultaneously using the colorimetric method and the fluorescence analysis.

In the present disclosure, the target material is not particularly limited, and may be a small-molecule material. As the small-molecule material, bisphenol A (BPA), bisphenol S (BPS), bisphenol F (BPF), β-estradiol, phthalate, thrombin, or the like may be used. In the present disclosure, the target material may be detected by selecting and using an aptamer capable of specifically binding thereto according to the type of the target material. In particular, in the case of BPA, β-estradiol, and thrombin, aptamers capable of binding to the materials are known in the art, and thus the target material may be readily detected using the method of the present disclosure.

The concentration of the target material may vary according to the type of the target material, and may generally range from 0.001 ng/ml to 10,000 ng/ml, or 0.01 ng/ml to 1,000 ng/ml.

A metal of metal nanoparticles may be gold or silver. The metal nanoparticles may exhibit mutually different colors according to an agglomerated or dispersed state.

In one embodiment, the metal nanoparticles may be surface-treated metal nanoparticles. In addition, in one embodiment, the metal nanoparticles may be particles stabilized by citrate. For example, when a single-stranded DNA aptamer is used as the aptamer, a base region of the single-stranded DNA aptamer may be easily adsorbed onto surfaces of the metal nanoparticles by van der Waals force.

The aptamer may be an aptamer capable of specifically binding to the target material. The aptamer may bind to metal nanoparticles to form an aptamer-gold nanoparticle complex, and may also bind to the target material to form an aptamer-target material complex.

The type of fluorescent dye is not particularly limited, and the fluorescent dye may be a dye that exhibits fluorescence when binding to an aptamer. As the fluorescent dye, SYBR Green, Gel Red, or Gel green may be used.

In addition, the salt may be sodium chloride (NaCl), and a salt-containing solution may be used for the convenience of use. In the present disclosure, a PBS buffer containing NaCl may be used.

In the present disclosure, process (A) is a process of reacting a sample including a target material with an aptamer-metal nanoparticle complex.

The aptamer-metal nanoparticle complex has a structure in which an aptamer is bound or adsorbed to metal nanoparticles, and the complex is present in the sample in a dispersed state. The aptamer can specifically bind to the target material, and thus the aptamer-metal nanoparticle complex reacts with the target material so that the aptamer is separated therefrom, and the separated aptamer may bind to the target material to thereby form an aptamer-target material complex.

In one embodiment, the metal nanoparticles may be surface-treated metal nanoparticles. In addition, in one embodiment, the metal nanoparticles may be particles stabilized by citrate. For example, when a single-stranded DNA aptamer is used as the aptamer, a base region of the single-stranded DNA aptamer may be easily adsorbed onto surfaces of the metal nanoparticles by van der Waals force.

In the present disclosure, process (B) is a process of adding a fluorescent dye to the reaction product of process (A) and measuring fluorescence.

The fluorescent dye may exhibit fluorescence when binding to the aptamer. When the fluorescent dye is added, the aptamer-metal nanoparticle complex reacts with the fluorescent dye so that the aptamer is separated therefrom, and the separated aptamer binds to the fluorescent dye, thereby exhibiting fluorescence.

However, the aptamer-target material complex formed in process (A) described above does not react with the fluorescent dye. SYBR Green used as the fluorescent dye, which is a cyanine-based dye, is a dye that binds to both dsNDA and ssDNA to thereby exhibit fluorescence. When the aptamer is present in a state of being bound to the surfaces of the metal nanoparticles, the dye binds to the aptamer since binding between SYBR Green and the aptamer is stronger than binding between the nanoparticles and the aptamer, thereby emitting fluorescence. In contrast, in a case in which the aptamer reacts with the target material, binding between a dye and the aptamer is competitively inhibited since binding between the aptamer and the target material is strong, resulting in no fluorescence emission.

Fluorescence may be measured using a general measurement method in the art. Generally, fluorescence intensity (fluorescence value) F may be calculated by Equation Fn/Fo, wherein Fo denotes a fluorescence value at a particular wavelength of a sample not including the target material, and Fn denotes a fluorescence value at a particular wavelength of an experimental group including the target material. The measurement wavelength may vary according to the type of a target material and the type of used fluorescent dye.

In the above process, as the concentration of the target material increases, fluorescence intensity decreases, and, as the concentration of the target material decreases, fluorescence intensity increases.

In one embodiment, when BPA is used as the target analyte, a fluorescence value may be calculated at a wavelength of 525 nm.

In the present disclosure, process (C) is a process of adding a salt to the reaction product of process (B) and measuring absorbance.

In the above process, when the salt is added to the reaction product, unbound metal nanoparticles agglomerate with each other, resulting in a color change.

In one embodiment, when gold nanoparticles are used as the metal nanoparticles, gold nanoparticles in a dispersed state exhibit red color, and agglomerated gold nanoparticles exhibit blue color. When the salt is added to the reaction product of process (B), an aptamer-gold nanoparticle complex is in a dispersed state, whereas gold nanoparticles agglomerate with each other to thereby exhibit blue color.

In the present disclosure, the presence or absence of the target material may be detected by measuring absorbance for such a color change, and furthermore, the target material may be quantified. The absorbance may be measured using a general measurement method in the art, and may be represented by Equation ODx/ODy, wherein x and y denote particular wavelengths. The measurement wavelengths may vary according to the type of target analyte, the type of metal nanoparticles, and the like.

In the above process, as the concentration of the target material increases, the absorbance increases, and as the concentration of the target material decreases, the absorbance decreases.

In one embodiment, when BPA is used as the target analyte, the absorbance may be represented by Equation $OD_{650}/OD_{530}$.

The present disclosure may also provide a method of quantifying a target material to be detected.

The quantification method may be performed using the above-described detection method, and particularly, a fluorescence value and an absorbance according to the concentration of the target material may be measured.

Fluorescence•absorbance of Equation 1 below may be calculated using the fluorescence value and the absorbance, and changes in the fluorescence, absorbance according to concentration may be used as a standard curve for quantification of the target material, thereby quantifying the target material.

Fluorescence•absorbance={(ODx/ODy)n−(ODx/ODy)o}/(Fn/Fo)   <Equation 1>

In Equation 1. ODx denotes absorbance at x nm. ODy denotes absorbance at y nm. (ODx/ODy)o and Fo denote an absorbance ratio and a fluorescence value, respectively, of a sample not including the target material (e.g., w.o.EDC sample), and (ODx/ODy)n and Fn denote an absorbance ratio and a fluorescence value, respectively, of a sample including the target material.

In the fluorescence and absorbance, the measurement wavelengths may vary according to the type of the target material, the type of metal nanoparticles, and the like.

In one embodiment, when BPA is used as the target analyte, fluorescence•absorbance may be calculated by Equation 2 below.

Fluorescence•absorbance={($OD_{650}/OD_{530}$)n−($OD_{650}/OD_{530}$)o}/(Fn/Fo)   <Equation 2>

In Equation 2, $OD_{650}$ denotes absorbance at 650 nm, $OD_{530}$ denotes absorbance at 530 nm, ($OD_{650}/OD_{530}$)o and Fo denote an absorbance ratio and a fluorescence value, respectively, of a sample not including BPA (e.g., w.o.EDC sample), and ($OD_{650}/OD_{530}$)n and Fn denote an absorbance ratio and a fluorescence value, respectively, of a sample including BPA.

In the present disclosure, to measure the concentration of a target material of a sample including the target material, fluorescence, absorbance of the sample may be calculated, and then may be substituted for the above-described standard curve to thereby measure the concentration of the target material.

The present disclosure also provides a kit for detecting and quantifying a target material.

The kit includes an aptamer-metal nanoparticle complex and a fluorescent dye. In the kit, the aptamer can specifically bind to the target material, and the fluorescent dye may exhibit fluorescence when binding to the aptamer.

In the present disclosure, the target material may be detected and quantified using the kit and the above-described detection and quantification methods.

Hereinafter, the present disclosure will be described in detail with reference to the following examples. However, these examples are provided for illustrative purposes only and are not intended to limit the scope of the present disclosure.

EXAMPLES

Preparation Example 1. Synthesis of Gold Nanoparticles

Gold nanoparticles were synthesized through the following method.

A round bottom flask was prepared by washing with aqua regia (9 ml of hydrochloric acid and 1 ml of nitric acid). HAuCl4 powder (Sigma Aldrich) was prepared at a concentration of 300 mM, and sodium citrate was prepared at 2%.

A magnetic bar was put in 55 ml of distilled water (DW) and the water was boiled on a hot plate under a hood. When the water started boiling, 100 µl of HAuCl4 was added thereto and after 10 seconds, 1 ml of sodium citrate was added to the resulting solution. The solution was maintained for about 15 minutes until the solution turned red, i.e., wine color. When the solution turned red, the heat source was removed and the resulting solution was cooled to room temperature and stored at 4° C., thereby completing the synthesis of gold nanoparticles.

The size of the gold nanoparticles was measured using a scatteroscope. 100 µl of the prepared solution was put in a cuvette and subjected to measurement for 5 minutes a total of five times, and an average of the measurement values was obtained.

As a result, it was calculated that 50 ml of gold nanoparticles having a particle diameter of about 28.34 nm and a concentration of about 0.85 nM was synthesized.

Preparation Example 2. Aptamer Sequence

The sequences of the aptamers used in the present disclosure are as follows:

Modified aptamer (44 mer, Truncated aptamer): 5'-CGGTGGGTGGTCAGGTGGGATAGCGTTCCGCGTATGGCCCAGCG-3'; and Full Length BPA aptamer (63 mer); Oligonucleotides 2011, 21(2); 85: 5'-CCG GTG GGT GGT CAG GTG GGA TAG CGT TCC GCG TAT GGC CCA GCG CAT CAC GGG TTC GCA CCA-3'.

The aptamers used in the present disclosure are bisphenol A (BPA) aptamers capable of binding to BPA as illustrated in FIG. 2.

The aptamers were prepared by boiling at 95° C. for 10 minutes and rapidly cooling on ice for 10 minutes.

Experimental Example 1. Detection of BPA (1) Method

A 100 µM aptamer (the modified aptamer of Preparation Example 2), tertiary distilled water, 20 mM Tris buffer (Tris HCl, pH 7.4), the gold nanoparticles prepared according to Preparation Example 1, BPA, 100×SYBR Green I, and 4×PBS were prepared.

BPA was dissolved in 100% ethanol at a concentration of 100 mM and diluted in tertiary distilled water before use. In the case of 100×SYBR Green I, a reagent purchased at 10000× was diluted in DMSO to 100× and freeze-stored, and melted at room temperature before use.

150 µl of the gold nanoparticles. 40 µl of Tris buffer, and 0.6 µl of the aptamer were pre-mixed in amounts to be added to all wells, and then 190 µl of the resulting solution was distributed into a transparent 96-well plate. Subsequently, a BPA sample to be analyzed was added at 10 µl per well (10 µl of the analysis sample with respect to a total volume of 200 µl).

The resulting solution was maintained at room temperature for 10 minutes, and then SYBR was diluted with distilled water to 1×, and the resulting SYBR solution was added thereto at 100 µl per well and mixed. Immediately thereafter, fluorescence was measured using Varioskan (Thermo Fisher Scientific). Fluorescence measurement was performed from 505 nm to 600 nm by excitation at 485 nm (a peak at 525 nm).

4×PBS was added to the measurement-completed sample at 10 µl per well, and the resulting sample was maintained for 5 minutes to 15 minutes until there was no longer any color change in the sample. Absorbance was measured using Varioskan (Thermo Fisher Scientific) from 450 nm to 800 nm.

(2) Results

Fluorescence•absorbance (y) was calculated by Equation below.

$$y=\{(OD_{650}/OD_{530})n-(OD_{650}/OD_{530})o\}/(Fn/Fo)$$

FIG. 1 is a diagram illustrating a method of detecting BPA, according to the present disclosure. As illustrated in FIG. 1, the greater the amount of BPA, the lower the fluorescence and the higher the absorbance $A_{650}/A_{530}$. In contrast, it can be confirmed that a BPA-free sample exhibits high fluorescence and a small $A_{650}/A_{530}$ value.

Experimental Example 2. Measurement of Suitability of Concentration Ratio of Aptamer and Gold Nanoparticles (1) Method 160 µl of gold nanoparticles was put into a transparent 96-well plate, and an aptamer (modified aptamer and full length aptamer were used) was added thereto to a final concentration of 0 nM to 1.000 nM. The final volume was 200 pd and the remainder was adjusted with DW. Binding was allowed to occur for 10 minutes, followed by agglomeration of the gold nanoparticles using a 12.5 mM NaCl solution, and the resulting solution was maintained for about 10 minutes until there was no longer any color change in the solution. When the color of the solution was changed, absorbance was measured using Varioskan (Thermo Fisher Scientific) from 450 nm to 800 nm to analyze color.

(2) Results

An absorbance ratio was used to analyze results (see FIG. 3).

When gold nanoparticles are agglomerated with each other, the agglomerated gold nanoparticles turn blue, and absorbance of the gold nanoparticles is decreased at 520 nm and is increased at 620 nm. Through this, it can be confirmed that the modified aptamer can completely protect gold at a concentration of 400 nM, whereas the full length aptamer can completely protect gold at a concentration of 1,000 nM.

That is, it can be confirmed that the modified aptamer has a more excellent capability of protecting gold than that of the full length aptamer.

Experimental Example 3. Examination of Reaction of Aptamer-Gold Nanoparticles with respect to BPA (1) Method A 100 µM aptamer (the modified aptamer of Preparation Example 2), tertiary distilled water, 20 mM Tris buffer (Tris HCl, pH 7.4), the gold nanoparticles prepared according to Preparation Example 1, BPA, and 1M NaCl were prepared.

BPA was dissolved in 100% ethanol at a concentration of 100 mM and diluted in tertiary distilled water before use.

In particular, 150 µl of the gold nanoparticles, 40 µl of Tris buffer (pH 7.4), and 0.6 µl of the aptamer were pre-mixed in amounts to be added to all wells, and then the resulting solution was distributed into a transparent 96-well plate at 190 µl per well. Subsequently, 10 µl of an environmental hormone (BPA) sample to be analyzed was added to each well. The resulting solution was maintained at room temperature for 10 minutes, 10 µl of 1M NaCl was then added to each well and the resulting solution was maintained at room temperature for 15 minutes until there was no longer any color change in the solution, and then the size of the gold nanoparticles was measured using Scatteroscope I (K-ONE) and a dark field optical microscope (CytoViva).

Meanwhile, an experimental group including only DW instead of BPA and an experimental group including 2,000 ng/mL of BPA were prepared. In addition, a control not including an aptamer and a salt was prepared. Water was added to the aptamer- or salt-free control to conduct an experiment.

(2) Results

The results are illustrated in FIG. 4.

FIG. 4-1 illustrates measurement results of the size of the gold nanoparticles according to the presence or absence of BPA, and FIG. 4-2 illustrates microscopic results of the size of the gold nanoparticles according to the presence or absence of BPA.

The concentration of BPA in the experimental group was $1.00 \times 10^2$ ng/ml.

From the results shown in FIGS. 4-1 and 4-2, it can be confirmed that the size of the gold nanoparticles is changed by the salt in the presence of $1.00 \times 10^2$ ng/ml of BPA. That is, BPA may be effectively sensed and detected using the method of the present disclosure.

Experimental Example 4. Quantitative Analysis of BPA and Examination of BPA Specificity (1) Method An 100 µM aptamer (the modified aptamer of Preparation Example 2), tertiary distilled water, 20 mM Tris buffer (Tris HCl, pH 7.4), the gold nanoparticles prepared according to Preparation Example 1, environmental hormones (BPA, BPS, BPF, and phthalate), 100×SYBR Green I, and 4×PBS were prepared.

All the environmental hormones were dissolved in 100% ethanol at a concentration of 100 mM, and diluted in tertiary distilled water before use. In the case of 100×SYBR Green I, a reagent purchased at 10000× was diluted to 100× with DMSO and freeze-stored, and melted at room temperature before use.

As experimental groups, a group including only DW instead of the environmental hormones, and groups including the environmental hormones at a concentration ranging from $1.00 \times 10^{-2}$ ng/ml to $1.00 \times 10^4$ ng/ml by an increment of 100-fold, i.e., from 1.00E-2 ng/ml to 1.00E+4 ng/ml, were prepared. In addition, an aptamer-free control was prepared. Water was added to the aptamer-free control to conduct an experiment.

In particular, 150 µl of the gold nanoparticles, 40 µl of Tris buffer (pH 7.4), and 0.6 µl of the aptamer were pre-mixed in amounts to be added to all wells, and then the resulting solution was distributed into a transparent 96-well plate at 190 µl per well. Subsequently, 10 µl of an environmental hormone sample to be analyzed was added to each well. The resulting solution was maintained at room temperature for 10 minutes, and then SYBR was diluted to 1× with distilled water, and 100 μl of the resulting SYBR solution was added to each well and mixed. Immediately thereafter, fluorescence was measured using Varioskan (Thermo Fisher Scientific).

Fluorescence measurement was performed from 505 nm to 600 nm by excitation at 485 nm. 10 d/well of 4×PBS was added to the measurement-completed sample, and the resulting sample was maintained for 5 minutes to 15 minutes until there was no longer any color change in the sample. Absorbance was measured using Varioskan (Thermo Fisher Scientific) from 450 nm to 800 nm.

(2) Results

The results are illustrated in FIGS. 5 and 6.

In FIGS. 5 and 6, fluorescence, absorbance was calculated by Equation $\{(OD_{650}/OD_{530})n-(OD_{650}/OD_{530})o\}/(Fn/Fo)$. In addition, the calculation results were represented as a graph with the exception of zero on a logarithmic scale to analyze results.

FIG. 5 illustrates measurement results of BPA according to concentration. The BPA was measured at a concentration ranging from $1.00×10-3$ ng/ml to $1.00×101$ ng/ml.

Through the results in FIG. 5, it is confirmed that BPA having a concentration ranging from 0.001 ng/ml to 10 ng/ml can be detected and quantitatively measured using the method according to the present disclosure. That is, when the method according to the present disclosure is used, a low concentration of BPA may be effectively detected, and this may be used as a standard curve to thereby detect BPA in an unidentified sample.

In addition, FIG. 6 illustrates measurement results of various types of environmental hormones.

From the results in FIG. 6, it is confirmed that BPA can be selectively measured using the method according to the present disclosure. However, it can also be confirmed that the method according to the present disclosure has reactivity with respect to other environmental hormones having similar structures, although the reactivity is weaker than that with respect to BPA.

Experimental Example 5. Measurement of BPA Using Receipt (1) Method

As receipt samples, a BPA-containing general receipt (Normal) and BPA-free receipt transfer paper (BPA free) were used.

Each receipt paper having a size of 10 cm×4 cm was put in 48 ml of tertiary distilled water and dissolved therein at room temperature for 30 minutes. The receipt sample was prepared by dilution with tertiary distilled water to 1/500, and 10 μl of the diluted sample was used for detection (see FIG. 11).

The BPA measurement method was performed in the same manner as in Experimental Example 3, and the results thereof are illustrated in FIG. 7.

(2) Results

Fluorescence•absorbance of each of the Normal receipt and the BPA-free receipt was calculated, and the results are illustrated as a graph in FIG. 7.

In addition, as a result of calculating concentration by substituting the calculated fluorescence, absorbance for the standard curve described in Experimental Example 3, the concentration of BPA in the Normal receipt was measured to be 6.68 ng/ml. As a result of multiplying this by the dilution factor, the actual concentration was calculated to be 6.68 (ng/ml)×500×20, i.e., 66,800 ng/ml, i.e., 66.8 μg/ml.

The BPA-containing general receipt (Normal) was measured by high-performance liquid chromatography (HPLC) (see FIG. 8), and as a result of measurement, the concentration was measured to be 61 μg/ml.

That is, it was seen that the BPA measurement method according to the present disclosure exhibited high accuracy similar to that of HPLC measurement.

From these results, it can be confirmed that the method of detecting and quantifying a target material, according to the present disclosure, is effective in quantifying the concentration of the target material and enables quantification within a short period of time.

Meanwhile, when the same calculation method was applied to the BPA-free receipt, the BPA-free receipt exhibited a lower value than the measurement range.

Comparative Experimental Example 1.
Measurement of BPA Using FAM-Aptamer (1) Method A 100 μM aptamer, tertiary distilled water, 40 μl of 20 mM Tris-HCl buffer (pH 7.4), citrate-gold nanoparticles, BPA, and 4×PBS were prepared. At this time, the aptamer was an FAM aptamer obtained by labeling the modified aptamer of Preparation Example 2 with fluorescence.

FAM aptamer-coated gold nanoparticles including 150 μl of gold nanoparticles, 40 td of Tris buffer, and 0.6 μl of the FAM-aptamer were prepared, and were distributed into a transparent 96-well plate at 190 μl per well. Subsequently, 10 μl of a BPA sample to be analyzed was added to each well (10 μl of the analysis sample with respect to a total volume of 200 μl).

The resulting solution was maintained at room temperature for 30 minutes, followed by addition of 10 td of 4×PBS thereto, and maintained for 10 minutes to 15 minutes to allow the gold nanoparticles to be agglomerated with each other so that the color of the solution was changed. When the color of the solution was completely changed, absorbance thereof was measured at 450 nm to 800 nm using Varioskan (Thermo Fisher Scientific) and the fluorescence intensity of FAM exhibiting maximum fluorescence at 520 nm was measured by excitation at 485 nm.

(2) Results

The measurement results are illustrated in FIG. 9.

In FIG. 9, $F=Fn-F0/F0$ was used as a general equation of fluorescence. In the general equation, Fn is a fluorescence value at 520 nm of the experimental group, and F0 is a fluorescence value at 520 nm of the BPA-free sample.

As the concentration of BPA increases, the FAM-aptamer binds to BPA and separates from the gold nanoparticles, and fluorescence (FAM) of the aptamer is beyond the quenching effect of gold nanoparticles, resulting in increased fluorescence intensity.

Comparative Experimental Example 2.
Measurement of BPA of Receipt Sample Using FAM Aptamer (1) Method The same types of receipts as those used in Experimental Example 4, i.e., Normal (BPA) and BPA free, were used. Each receipt having a size of 10 cm×4 cm was put in 48 ml of water and an environmental hormone in the receipt was dissolved therein for 30 minutes, and the resulting sample was diluted with water to 1/250 for measurement.

The BPA measurement test was performed in the same manner as in an experiment using a standard reagent. That is, 10 µl of the receipt sample was added instead of a standard concentration, i.e., 10 µl of BPA and an experiment was carried out.

(2) Results

The measured fluorescence intensity was substituted for a graph obtained using the standard reagent (middle graph in FIG. 9) to calculate the concentration of BPA included in the Normal receipt.

As a result of calculation, the concentration of BPA was measured to be 323.4 µg/ml.

This shows a very significant difference from the HPLC measurement results (concentration: 61 µg/ml).

That is, it was confirmed that the comparative experimental examples using FAM-aptamer and not using a fluorescent dye had very low accuracy and sensitivity compared to the method according to the present disclosure. In the case of the method according to the present disclosure, fluorescence and absorbance are independently measured, and fluorescence and absorbance signals may compensate for each other through an analysis method different from an existing method, i.e., a fluorescence×absorbance method, resulting in increased analysis accuracy.

While the invention has been shown and described with reference to certain exemplary embodiments thereof, it will be understood by those skilled in the art that various changes in form and details may be made therein without departing from the spirit and scope of the invention as defined by the appended claims.

What is claimed is:

1. A method of detecting a target material, the method comprising:
    reacting a sample comprising a target material with an aptamer-metal nanoparticle complex; wherein the aptamer-metal nanoparticle complex reacts with the target material when present in the sample so as for the aptamer to be separated from the complex, and the separated aptamer forms an aptamer-target material complex by binding to the target material;
    adding a fluorescent dye to a reaction product of the reacting and measuring fluorescence; wherein either the aptamer-target material complex formed when the sample contains the target material does not react with the fluorescent dye so that no fluorescence is produced, or the aptamer-metal nanoparticle complex reacts with the fluorescent dye so as for the aptamer to be separated from the complex when no target material is present in the sample, and the separated aptamer exhibits fluorescence by binding to the fluorescent dye; and
    adding a salt to a reaction product of the adding and measuring absorbance, wherein metal nanoparticles that do not have an aptamer bound exhibit a color change by being agglomerated with each other and the color change is measured by absorbance.

2. The method of claim 1, wherein the target material is one selected from bisphenol A (BPA), bisphenol S (BPS), bisphenol F (BPF), β-estradiol, phthalate, and thrombin.

3. The method of claim 1, wherein the target material has a concentration ranging from 0.001 ng/ml to 10,000 ng/ml.

4. The method of claim 1, wherein in metal nanoparticles, a metal is gold or silver.

5. The method of claim 1, wherein the fluorescent dye is one selected from SYBR Green, Gel Red, and Gel green.

6. The method of claim 1, wherein the salt is sodium chloride.

7. A method of quantifying a target material to be detected, the method comprising:
    measuring a fluorescence value and absorbance according to a concentration of a target material to be detected, using the method according to claim 1;
    calculating fluorescence•absorbance of Equation 1 below by using the fluorescence value and the absorbance; and
    using changes in fluorescence•absorbance according to concentration as a standard curve for quantification of the target material, $$\text{Fluorescence·absorbance} = \{(OD_x/OD_y)n - (OD_x/OD_y)o\}/(Fn/Fo) \quad \text{<Equation 1>}$$

wherein, in Equation 1, $OD_x$ denotes absorbance at x nm, $OD_y$ denotes absorbance at y nm, $(OD_x/OD_y)o$ and Fo denote an absorbance ratio and a fluorescence value, respectively, of a sample not comprising the target material, and $(OD_x/OD_y)n$ and Fn denote an absorbance ratio and a fluorescence value, respectively, of a sample comprising the target material.

8. The method of claim 7, wherein, when the target material is bisphenol A, the fluorescence•absorbance is calculated by Equation 2 below:

$$\text{Fluorescence·absorbance} = \{(OD_{650}/OD_{530})n - (OD_{650}/OD_{530})o\}/(Fn/Fo) \quad \text{<Equation 2>}$$

wherein, in Equation 2, $OD_{650}$ denotes absorbance at 650 nm, $OD_{530}$ denotes absorbance at 530 nm, $(OD_{650}/OD_{530})o$ and Fo denote an absorbance ratio and a fluorescence value, respectively, of a sample not comprising bisphenol A, and $(OD_{650}/OD_{530})n$ and Fn denote an absorbance ratio and a fluorescence value, respectively, of a sample comprising bisphenol A.

9. The method of claim 7, wherein a concentration of a target material in the sample comprising the target material is obtained by finding the calculated fluorescence-absorbance of the sample on the standard curve and then matching with a corresponding concentration of the target material that results in said fluorescence-absorbance.

* * * * *